United States Patent [19]
Gilbert et al.

[11] 4,280,513
[45] Jul. 28, 1981

[54] TOOL AND METHOD FOR ATTACHING ELECTRODE TO BODY TISSUE

[76] Inventors: Richard S. Gilbert, 1144 Sonoma Ave., Ste. 111; Douglas W. Cardozo, 1111 Sonoma Ave., Ste. 302, both of Santa Rosa, Calif. 95405

[21] Appl. No.: 110,204

[22] Filed: Jan. 7, 1980

[51] Int. Cl.³ ............................................. A61N 1/04
[52] U.S. Cl. .................................................. 128/785
[58] Field of Search ............... 128/303 R, 419 P, 784, 128/785

[56] References Cited
U.S. PATENT DOCUMENTS

| | | | |
|---|---|---|---|
| 3,875,947 | 4/1973 | Jula et al. | 128/419 P |
| 3,943,936 | 3/1976 | Rasor et al. | 128/419 P |

OTHER PUBLICATIONS

"Mechanical Engineering", Jan. 1967, p. 48.

Primary Examiner—William E. Kamm
Attorney, Agent, or Firm—Flehr, Hohbach, Test

[57] ABSTRACT

Tool and method for attaching an electrode having a rigid screw-like conductor to the heart or other body tissue. The tool has an elongated handle and a driving head mounted for rotation about an axis generally perpendicular to the handle. The electrode is placed on the driving head with the screw-like conductor aligned with the axis of the driving head and the flexible electrical lead of the electrode wrapped about the driving head. The lead is pulled in a tangential direction to rotate the head and drive the helical conductor into the body tissue.

17 Claims, 9 Drawing Figures

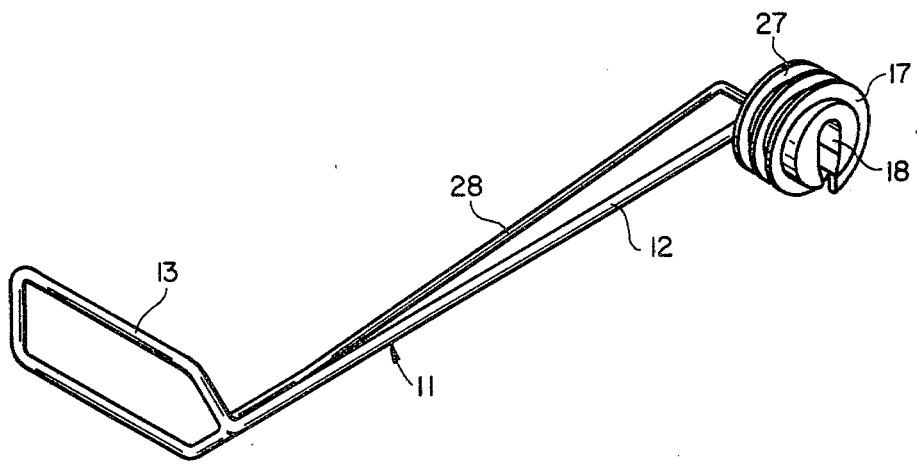
FIG_1
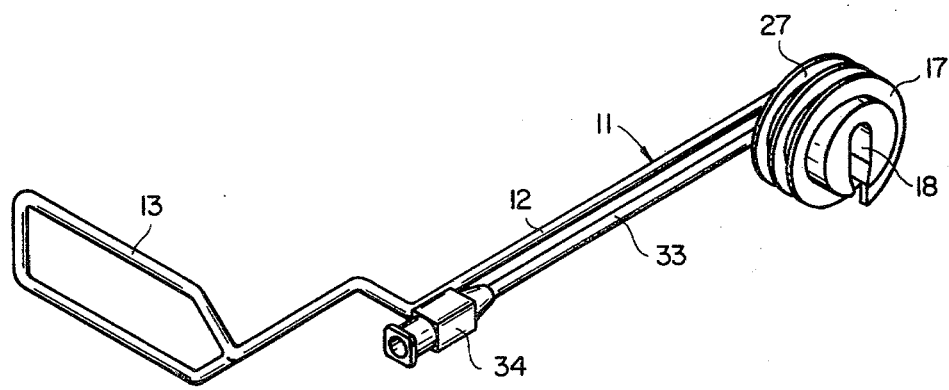
FIG_2
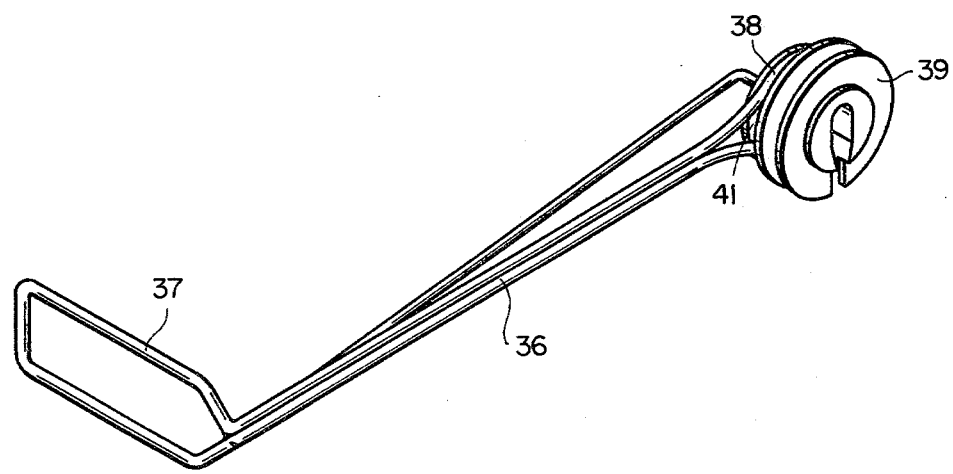
FIG_3

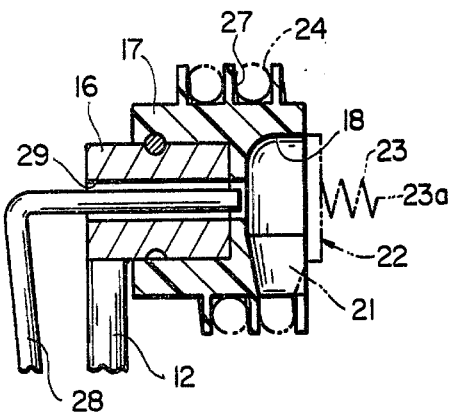
FIG_4
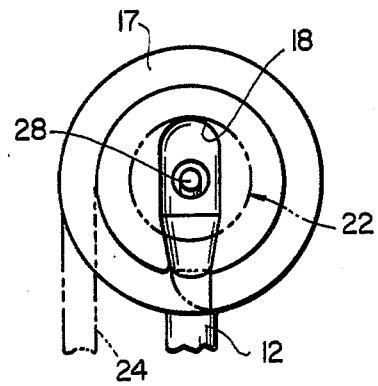
FIG_5
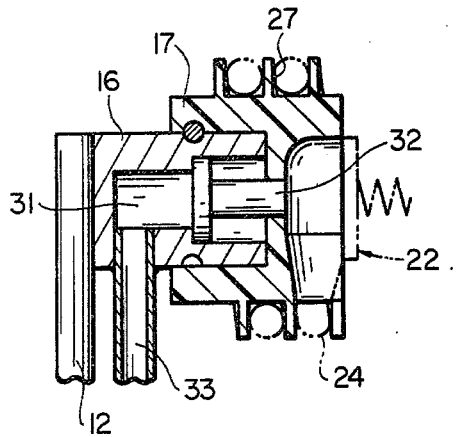
FIG_6
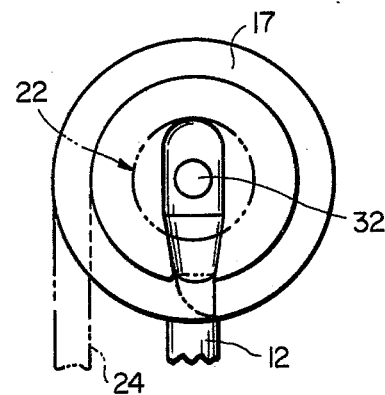
FIG_7
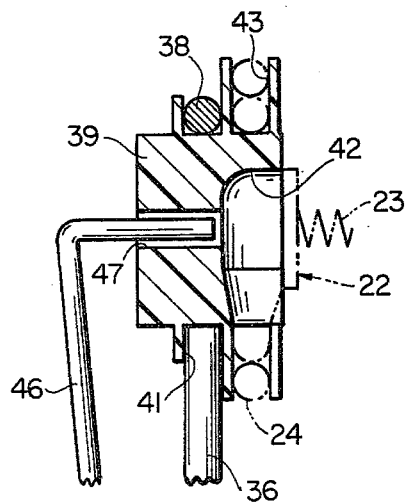
FIG_8
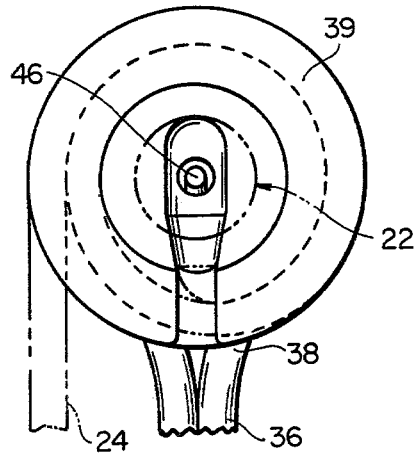
FIG_9

TOOL AND METHOD FOR ATTACHING ELECTRODE TO BODY TISSUE

This invention pertains generally to medical appliances and more particularly to a tool and method for attaching an electrode to the heart or other body tissue.

Electrodes for attachment to the heart and other organs of the body commonly have a sharply pointed helical electrode or conductor which is screwed into the tissue. Such electrodes are usually implanted with a screwdriver-like tool having an elongated shaft for axial engagement with the electrodes to drive the same into the tissue. Examples of electrodes and tools of this type are found in U.S. Pat. Nos. 3,737,579 and 3,875,947. These tools generally require direct, unobstructed access to the surface of the tissue to which the electrode is to be attached, and they are not suitable for use in attaching electrodes to the side of the heart or in other areas where a direct, head-on approach is not posssible.

It is in general an object of the invention to provide a new and improved tool and method for attaching an electrode to the heart or other body tissue.

Another object of the invention is to provide a tool and method of the above character whereby the electrode can be attached to the side of the heart or other organ.

These and other objects are achieved in accordance with the invention by providing a tool having an elongated handle and a driving head mounted for rotation about an axis generally perpendicular to the handle. The electrode is placed on the driving head with the screw-like contact aligned with the axis of the driving head and the flexible electrical lead of the electrode wrapped about the driving head. The pointed tip of the helical conductor is pressed against the body tissue, and the electrical lead is pulled in a tangential direction to rotate the driving head and drive the screw-like conductor into the tissue.

FIGS. 1-3 are isometric views of three embodiments of electrode attaching tools incorporating the invention.

FIG. 4 is an enlarged fragmentary sectional view of the electrode attaching tool of FIG. 1.

FIG. 5 is a side elevational view of the portion of the tool shown in FIG. 4.

FIG. 6 is an enlarged fragmentary sectional view of the electrode tool of FIG. 2.

FIG. 7 is a side elevational view of the portion of the tool shown in FIG. 6.

FIG. 8 is an enlarged fragmentary sectional view of the electrode attaching tool of FIG. 3.

FIG. 9 is a side elevational view of the portion of the tool shown in FIG. 8.

As shown in FIG. 1, the tool for attaching an electrode includes a handle 11 fabricated of a rigid wire such as stainless steel. The handle includes an elongated shaft 12 with a generally rectangular loop 13 formed at one end thereof and lying in a plane generally perpendicular to the axis of the shaft. A cylindrical hub 16 is affixed to the handle at the other end of the shaft, with the axis of the hub generally perpendicular to the axis of the shaft. A driving head 17 is rotatively mounted on the hub for rotation about the axis of the hub. The driving head has an axially facing socket 18 formed in the outer end thereof for receiving the body 21 of an electrode 22. The electrode body has a somewhat resilient outer covering of an electrically insulative material which is relatively inert with respect to the human body. The contour of socket 18 conforms generally to the contour of the electrode body, and the size of the socket is such that the electrode body can be pressed into the socket and gripped thereby.

The electrode also includes a rigid helical electrode or conductor 23, and a flexible electrical lead 24 which is connected to the exposed conductor within the electrode body. The helical electrode has a sharply pointed tip 23a and is adapted to be screwed into the heart or other body tissue by rotation about the axis of the helix. The electrode is held by driving head 17 in such manner that the axis of the helical conductor is aligned with the axis of the driving head.

The driving head also includes a peripheral groove 27 for receiving one or more wrappings of electrode lead 24. The remaining portion of the lead extends in a generally tangential direction from the groove, and pulling on this portion of the lead causes the driving head to rotate about its axis. In the embodiment of FIG. 1, groove 27 is a helical groove with a pitch or sense opposite to that of helical conductor 23 so that the helical conductor will turn in the proper direction for insertion into the body tissue when the lead is pulled. The lead has a somewhat resilient layer of electrical insulation, and the width of groove 27 is slightly less than the diameter of the lead so that the lead is gripped by the side walls of the groove. The lead is preferably wrapped about the driving head a number of turns corresponding to the number of convolutions in the helical conductor 23 so that the conductor will be fully driven when the lead is fully extended.

Means is provided for separating the tool from the electrode after the electrode has been driven. In the embodiment of FIG. 1, this means includes a manually operable release rod 28, one end of which is affixed to handle 11 adjacent to loop 13. The release rod extends from the point of attachment toward driving head 17 and diverges rearwardly from shaft 12 as it approaches the driving head. The free end of the release rod extends in a forward direction through an axial bore 29 in hub 16 and the driving head. The release rod is fabricated of a relatively flexible material, and the forward tip of the rod is positioned slightly behind the rear wall of socket 18 when the rod is in its rest position. The rod is moved forward to engage the back side of the electrode body to disengage the driving head from the electrode.

Operation and use of the embodiment of FIG. 1, and therein the method of the invention, is as follows. The body of the electrode is pressed into socket 18, with screw-like conductor 23 extending axially from the driving head. The portion of lead 24 adjacent to the electrode body is wrapped about the driving head in groove 27. The tool is then positioned to press the tip of the electrode against the side wall of the heart or other body tissue, and the free end of lead 24 is pulled to impart rotation to driving head 17 and thereby drive the screw-like conductor into the tissue. Once the electrode has been implanted, release rod 28 is pressed forward to separate the driving head from the electrode.

The embodiment of FIG. 2 is generally similar to the embodiment of FIG. 1, and like reference numerals are used to designate corresponding elements in the two embodiments. In the embodiment of FIG. 2, however, hub 16 has an axially extending internal bore 31 in which a fluid operated piston 32 is mounted for engaging the back side of the electrode body for separating the driving head from the electrode. A hydraulic line 33 communicates with bore 31 and extends away from the driving head in a direction generally parallel to shaft 12. Line 33 terminates in a fitting 34 for connection to a pressurized source of fluid, not shown. Fitting 34 is affixed to shaft 12, and the shaft is offset rearwardly adjacent to the fitting to permit access to the fitting.

Operation and use of the embodiment of FIG. 2 is generally similar to that described above. In this embodiment, however, the driving head is separated from the electrode by applying pressurized fluid to line 33 to actuate the piston.

The embodiment of FIG. 3 has a bifurcated wire handle 36 with a generally rectangular loop 37 similar to loop 13 at one end thereof. At the other end, handle 36 has a generally circular loop 38 in which a driving head 39 is relatively mounted. The loop serves as a bearing and is received in a peripheral groove 41 in the cylindrical driving head. Driving head 39 includes a socket 42 similar to socket 18 for receiving the body of electrode 22. This driving head also includes a single annular peripheral groove 43 of a depth sufficient to receive a plurality of windings of the electrical lead 24 of the electrode. As illustrated, the screw-like conductor of the electrode has approximately two convolutions, and two windings of the lead are wrapped in groove 43.

A release rod 46 similar to release rod 28 is affixed to the handle adjacent to loop 37 and extends through a bore 47 in driving head 39 for engagement with the back side of the electrode body.

Operation and use of the embodiment of FIG. 3 is similar to that described above. In this embodiment, however, the portion of the lead adjacent to the electrode body is wrapped about the driving head in the single annular groove. As in the other embodiments, the lead is wrapped in a direction opposite to the sense of electrode conductor 23 will be rotated in the proper direction for insertion into the body tissue when the lead is pulled.

The invention has a number of features and advantages. It is easy to use and permits electrodes to be attached to portions of the body which are not accessible with the tools of the prior art.

It is apparent from the foregoing that a new and improved tool and method for attaching an electrode to the body tissue have been provided. While only certain presently preferred embodiments have been described, as will be apparent to those familiar with the art, certain changes and modifications can be made without departing from the scope of the invention as defined by the following claims.

What is claimed is:

1. In a tool for attaching an electrode to body tissue, said electrode having a body with a screw-like helical conductor and a flexible electrical lead extending therefrom: an elongated handle, a driving head rotatively mounted on the handle with means for engaging the body of the electrode and holding the same in a fixed position with the helical conductor extending along the axis of rotation, and means for receiving at least one wrapping of the electrical lead about the driving head in such manner that pulling on the lead imparts a rotation to the driving head for screwing the conductor into the body tissue.

2. The tool of claim 1 wherein the axis of rotation of the driving head is generally perpendicular to the axis of the handle.

3. The tool of claim 1 wherein the means for receiving the electrical lead comprises a peripheral groove in the driving head.

4. The tool of claim 1 wherein the means for receiving the electrical lead comprises a helical groove in the driving head.

5. The tool of claim 1 further including means carried by the handle for disengaging the driving head from the electrode body after the electrode has been attached to the body tissue.

6. The tool of claim 5 wherein the means for disengaging the driving head includes a manually operable release rod movable axially of the driving head for engaging the electrode body to effect separation of the driving head and the electrode.

7. The tool of claim 1 wherein the means for disengaging the driving head includes a fluid actuated piston movable axially of the driving head for engagement of the electrode body to effect separation of the driving head and the electrode.

8. The apparatus of claim 1 wherein the driving head is mounted for rotation about an axis generally perpendicular to the axis of the handle.

9. In apparatus for making electrical contact with body tissue: a handle, a driving head rotatively mounted on the handle, and an electrode mounted on the driving head with a helical screw-like conductor extending axially from the driving head for insertion into the tissue and a flexible electrical lead wrapped about the driving head and extending tangentially therefrom to be pulled upon to impart rotation to the driving head and thereby screw the conductor into the tissue.

10. The apparatus of claim 8 wherein the driving head includes a peripheral groove in which the cord is wrapped.

11. The apparatus of claim 8 further including means carried by the handle for disengaging the driving head from the electrode after the electrode has been attached to the tissue.

12. The apparatus of claim 11 wherein the means for disengaging the driving head includes a manually operable release rod movable axially of the driving head for engagement with the electrode body to effect separation of the driving head and the electrode.

13. The apparatus of claim 11 wherein the means for disengaging the driving head includes a fluid actuated piston movable axially of the driving head for engagement with the electrode body to effect separation of the driving head and the electrode.

14. In a tool for attaching an electrode having a screw-like helical conductor and a flexible electrical lead: an elongated handle, a generally cylindrical head mounted on the handle for rotation about the axis generally perpendicular to the axis of the handle. Means carried by the driving head for engaging the electrode for holding the same with the helical conductor extending axially from the driving head, a peripheral groove in the driving head for receiving the electrical lead of the electrode in a wrapped fashion such that pulling on the lead will rotate the driving head and the screw-like conductor of the electrode, and means carried by the handle for disengaging the driving head from the electrode.

15. The tool of claim 14 wherein the means for disengaging the driving head includes a manually operable release rod movable axially of the driving head for engagement with the electrode to effect separation of the driving head and the electrode.

16. The tool of claim 14 wherein the means for disengaging the driving head includes a fluid actuated piston movable axially of the driving head for engagement with the electrode to effect separation of the driving head and the electrode.

17. In a method utilizing a tool having a rotatable driving head for attaching an electrode to body tissue, said electrode having a body with a screw-like helical conductor and a electrical lead extending therefrom, the steps of: placing the electrode on the driving head with the helical conductor extending axially from the driving head, wrapping the electrical lead about the driving head, positioning the tool such that the tip of the helical conductor contacts the body tissue, and pulling the electrical lead from the driving head in a tangential direction while pressing the helical conductor against the tissue to rotate the driving head and drive the screw-like conductor into the tissue.

* * * * *